United States Patent
Markosyan

(10) Patent No.: US 9,474,296 B2
(45) Date of Patent: Oct. 25, 2016

(54) GLUCOSYL STEVIA COMPOSITION

(75) Inventor: Avetik Markosyan, Yerevan (AM)

(73) Assignee: PureCircle Sdn Bhd, Kuala Lumpur (MY)

(*) Notice: Subject to any disclaimer, the term of this patent is extended or adjusted under 35 U.S.C. 154(b) by 138 days.

(21) Appl. No.: 14/352,832

(22) PCT Filed: Aug. 28, 2012

(86) PCT No.: PCT/US2012/052659
§ 371 (c)(1),
(2), (4) Date: Aug. 18, 2014

(87) PCT Pub. No.: WO2013/058870
PCT Pub. Date: Apr. 25, 2013

(65) Prior Publication Data
US 2015/0030725 A1  Jan. 29, 2015

Related U.S. Application Data

(60) Continuation-in-part of application No. 13/567,707, filed on Aug. 6, 2012, now Pat. No. 8,647,844, which is a division of application No. 13/029,263, filed on Feb. 17, 2011, now Pat. No. 8,257,948.

(60) Provisional application No. 61/580,274, filed on Dec. 26, 2011, provisional application No. 61/548,818, filed on Oct. 19, 2011.

(51) Int. Cl.
| | |
|---|---|
| C12P 19/18 | (2006.01) |
| C12P 19/56 | (2006.01) |
| A23L 2/60 | (2006.01) |
| A23L 1/236 | (2006.01) |
| A23C 9/13 | (2006.01) |
| A21D 2/36 | (2006.01) |
| A61K 36/28 | (2006.01) |
| C12P 33/00 | (2006.01) |
| A21D 2/18 | (2006.01) |
| A21D 13/06 | (2006.01) |
| A61K 31/704 | (2006.01) |

(52) U.S. Cl.
CPC .......... *A23L 1/2366* (2013.01); *A21D 2/181* (2013.01); *A21D 2/36* (2013.01); *A21D 13/062* (2013.01); *A23C 9/1307* (2013.01); *A23L 2/60* (2013.01); *A61K 31/704* (2013.01); *A61K 36/28* (2013.01); *C12P 19/18* (2013.01); *C12P 19/56* (2013.01); *C12P 33/00* (2013.01); *A23V 2002/00* (2013.01)

(58) Field of Classification Search
None
See application file for complete search history.

(56) References Cited

U.S. PATENT DOCUMENTS

| | | |
|---|---|---|
| 3,723,410 A | 3/1973 | Persinos |
| 4,082,858 A | 4/1978 | Morita et al. |
| 4,171,430 A | 10/1979 | Matsushita et al. |
| 4,219,571 A | 8/1980 | Miyake |
| 4,361,697 A | 11/1982 | Dobberstein et al. |
| 4,454,290 A | 6/1984 | Dubois |
| 4,590,160 A | 5/1986 | Nishihashi et al. |
| 4,599,403 A | 7/1986 | Kumar |
| 4,612,942 A | 9/1986 | Dobberstein et al. |
| 4,657,638 A | 4/1987 | le Grand et al. |
| 4,892,938 A | 1/1990 | Giovanetto |
| 4,917,916 A | 4/1990 | Hirao et al. |
| 5,112,610 A | 5/1992 | Kienle |
| 5,576,042 A | 11/1996 | Fuisz |
| 5,779,805 A | 7/1998 | Morano |
| 5,962,678 A | 10/1999 | Payzant et al. |
| 5,972,120 A | 10/1999 | Kutowy et al. |
| 6,031,157 A | 2/2000 | Morita et al. |
| 6,080,561 A | 6/2000 | Morita et al. |
| 6,204,377 B1 | 3/2001 | Nishimoto et al. |
| 6,228,996 B1 | 5/2001 | Zhou et al. |
| 6,706,304 B1 | 3/2004 | Ishida et al. |
| 7,807,206 B2 | 10/2010 | Magomet et al. |
| 7,838,044 B2 | 11/2010 | Abelyan et al. |
| 7,862,845 B2 | 1/2011 | Magomet et al. |
| 8,257,948 B1 | 9/2012 | Markosyan |
| 8,318,459 B2* | 11/2012 | Markosyan ............ A61K 36/28 426/548 |
| 2002/1322320 | 9/2002 | Wang et al. |
| 2003/0161876 A1 | 8/2003 | Hansson et al. |
| 2003/0236399 A1 | 12/2003 | Zheng et al. |
| 2006/0083838 A1 | 4/2006 | Jackson et al. |

(Continued)

FOREIGN PATENT DOCUMENTS

| | | |
|---|---|---|
| BR | P10701736 | 7/2008 |
| CN | 1049666 | 3/1991 |

(Continued)

OTHER PUBLICATIONS

FAO/WHO "Combined Compendium of Food Additive Specifications" FAO JECFA Monographs 1, vol. 4, 2006, Food and Agricultural Organization of the United Nations, Rome.*

(Continued)

*Primary Examiner* — Robert Yamasaki
*Assistant Examiner* — Charles Zoltan Constantine
(74) *Attorney, Agent, or Firm* — Briggs and Morgan, P.A.; Audrey J. Babcock

(57) ABSTRACT

Glucosyl stevia compositions are prepared from steviol glycosides of *Stevia rebaudiana* Bertoni. The glucosylation was performed by cyclodextrin glucanotransferase using the starch as source of glucose residues. The compositions mainly comprise glucosyl derivatives with superior taste characteristics and can be used as sweetness enhancers, flavor enhancers and sweeteners in foods, beverages, cosmetics and pharmaceuticals.

12 Claims, 3 Drawing Sheets

(56) References Cited

U.S. PATENT DOCUMENTS

| | | |
|---|---|---|
| 2006/0134292 A1 | 6/2006 | Abelyan et al. |
| 2006/0142555 A1 | 6/2006 | Jonnala et al. |
| 2007/0082102 A1 | 4/2007 | Magomet et al. |
| 2007/0082103 A1 | 4/2007 | Magomet et al. |
| 2007/0116800 A1 | 5/2007 | Prakash |
| 2007/0116819 A1 | 5/2007 | Prakash |
| 2007/0116820 A1 | 5/2007 | Prakash |
| 2007/0116821 A1 | 5/2007 | Prakash |
| 2007/0116822 A1 | 5/2007 | Prakash |
| 2007/0116823 A1 | 5/2007 | Prakash |
| 2007/0116824 A1 | 5/2007 | Prakash |
| 2007/0116825 A1 | 5/2007 | Prakash |
| 2007/0116826 A1 | 5/2007 | Prakash |
| 2007/0116827 A1 | 5/2007 | Prakash |
| 2007/0116828 A1 | 5/2007 | Prakash |
| 2007/0116829 A1 | 5/2007 | Prakash |
| 2007/0116830 A1 | 5/2007 | Prakash |
| 2007/0116831 A1 | 5/2007 | Prakash |
| 2007/0116832 A1 | 5/2007 | Prakash |
| 2007/0116833 A1 | 5/2007 | Prakash |
| 2007/0116834 A1 | 5/2007 | Prakash |
| 2007/0116835 A1 | 5/2007 | Prakash |
| 2007/0116836 A1 | 5/2007 | Prakash |
| 2007/0116837 A1 | 5/2007 | Prakash |
| 2007/0116838 A1 | 5/2007 | Prakash |
| 2007/0116839 A1 | 5/2007 | Prakash |
| 2007/0116840 A1 | 5/2007 | Prakash |
| 2007/0116841 A1 | 5/2007 | Prakash |
| 2007/0128311 A1 | 6/2007 | Prakash |
| 2007/0134390 A1 | 6/2007 | Prakash |
| 2007/0134391 A1 | 6/2007 | Prakash |
| 2007/0224321 A1 | 9/2007 | Prakash |
| 2007/0292582 A1 | 12/2007 | Prakash et al. |
| 2008/0064063 A1 | 3/2008 | Brandle et al. |
| 2008/0102497 A1 | 5/2008 | Wong et al. |
| 2008/0107775 A1 | 5/2008 | Prakash |
| 2008/0107776 A1 | 5/2008 | Prakash |
| 2008/0107787 A1 | 5/2008 | Prakash |
| 2008/0108710 A1 | 5/2008 | Prakash |
| 2008/0111269 A1 | 5/2008 | Politi et al. |
| 2008/0226797 A1 | 9/2008 | Lee et al. |
| 2008/0292764 A1 | 11/2008 | Prakash et al. |
| 2008/0292765 A1 | 11/2008 | Prakash |
| 2008/0292775 A1 | 11/2008 | Prakash |
| 2008/0300402 A1 | 12/2008 | Yang et al. |
| 2009/0017185 A1 | 1/2009 | Catani |
| 2009/0053378 A1 | 2/2009 | Prakash |
| 2009/0074935 A1 | 3/2009 | Lee |
| 2009/0079935 A1 | 3/2009 | Harris et al. |
| 2009/0142817 A1 | 6/2009 | Norman et al. |
| 2009/0226590 A1 | 9/2009 | Fouache et al. |
| 2010/0011215 A1 | 1/2010 | Abelyan et al. |
| 2010/0055752 A1 | 3/2010 | Kumar |
| 2010/0056472 A1 | 3/2010 | Duan et al. |
| 2010/0099857 A1 | 4/2010 | Evans et al. |
| 2010/0057024 A1 | 5/2010 | Cavallini et al. |
| 2010/0120710 A1 | 5/2010 | Watanabe et al. |
| 2010/0137569 A1 | 6/2010 | Prakash et al. |
| 2010/0189861 A1 | 7/2010 | Abelyan et al. |
| 2010/0227034 A1 | 9/2010 | Purkayastha et al. |
| 2010/0255171 A1 | 10/2010 | Purkayastha et al. |
| 2010/0278993 A1 | 11/2010 | Prakash et al. |
| 2010/0316782 A1 | 12/2010 | Shi et al. |
| 2011/0030457 A1 | 2/2011 | Valery et al. |
| 2011/0033525 A1 | 2/2011 | Liu |
| 2011/0092684 A1 | 4/2011 | Abelyan et al. |
| 2011/0104353 A1 | 5/2011 | Lee |
| 2011/0111115 A1 | 5/2011 | Shi et al. |
| 2011/0124587 A1 | 5/2011 | Jackson et al. |
| 2011/0160311 A1 | 6/2011 | Prakash et al. |
| 2011/0189360 A1 | 8/2011 | Yoo et al. |
| 2011/0195169 A1 | 8/2011 | Markosyan et al. |
| 2012/0164678 A1 | 6/2012 | Stephanopoulos et al. |
| 2012/0214752 A1 | 8/2012 | Markosyan |

FOREIGN PATENT DOCUMENTS

| | | | |
|---|---|---|---|
| CN | 1100727 | 3/1995 | |
| CN | 1112565 | 11/1995 | |
| CN | 1192447 | 9/1998 | |
| CN | 1238341 | 12/1999 | |
| CN | 1349997 | 5/2002 | |
| CN | 101200480 | 6/2008 | |
| JP | 52005800 | 1/1977 | |
| JP | 52083731 | 7/1977 | |
| JP | 52100500 | 8/1977 | |
| JP | 52136200 | 11/1977 | |
| JP | 54030199 | 3/1979 | |
| JP | 54132599 | 10/1979 | |
| JP | 55039731 | 3/1980 | |
| JP | 55081567 | 6/1980 | |
| JP | 55092400 | 7/1980 | |
| JP | 55120770 | 9/1980 | |
| JP | 55138372 | 10/1980 | |
| JP | 55159770 | 12/1980 | |
| JP | 55162953 | 12/1980 | |
| JP | 56099768 | 8/1981 | |
| JP | 56109568 | 8/1981 | |
| JP | 56121453 | 9/1981 | |
| JP | 56121454 | 9/1981 | |
| JP | 56121455 | 9/1981 | |
| JP | 56160962 | 12/1981 | |
| JP | 57002656 | 1/1982 | |
| JP | 57005663 | 1/1982 | |
| JP | 57046998 | 3/1982 | |
| JP | 57075992 | 5/1982 | |
| JP | 57086264 | 5/1982 | |
| JP | 58020170 | 2/1983 | |
| JP | 58028246 | 2/1983 | |
| JP | 58028247 | 2/1983 | |
| JP | 58212759 | 12/1983 | |
| JP | 58212760 | 12/1983 | |
| JP | 59045848 | 3/1984 | |
| JP | 62166861 | 7/1987 | |
| JP | 63173531 | 7/1988 | |
| JP | 1131191 | 5/1989 | |
| JP | 3262458 | 11/1991 | |
| JP | 6007108 | 1/1994 | |
| JP | 6192283 | 7/1994 | |
| JP | 7143860 | 6/1995 | |
| JP | 7177862 | 7/1995 | |
| JP | 8000214 | 1/1996 | |
| JP | 9107913 | 4/1997 | |
| JP | 2000236842 | 9/2000 | |
| JP | 2002262822 | 9/2002 | |
| JP | 2010516764 | 5/2010 | |
| KR | 20070067199 | 6/2007 | |
| KR | 20080071605 | 8/2008 | |
| KR | 20090021386 | 3/2009 | |
| RU | 2111969 | 5/1998 | |
| RU | 2123267 | 12/1998 | |
| RU | 2156083 | 9/2000 | |
| RU | 2167544 | 5/2001 | |
| RU | 2198548 | 2/2003 | |
| WO | 2005089483 | 9/2005 | |
| WO | 2006072878 | 7/2006 | |
| WO | 2006072879 | 7/2006 | |
| WO | 2008091547 | 7/2008 | |
| WO | 2009108680 | 9/2009 | |
| WO | 2010118218 | 10/2010 | |
| WO | 2011059954 | 5/2011 | |
| WO | 2011153378 | 12/2011 | |
| WO | 2012082493 | 6/2012 | |
| WO | 2012082677 | 6/2012 | |
| WO | WO 2012125991 A2 * | 9/2012 | ........... A23L 1/2366 |
| WO | 2013022989 | 2/2013 | |

OTHER PUBLICATIONS

Shi, et al., "Synthesis of bifunctional polymeric adsorbent and its application in purification of Stevia glycosides", Reactive & Functional Polymers, vol. 50 2002, 107-116.

(56) References Cited

OTHER PUBLICATIONS

Shibata et al., "Glucosylation of Steviol and Steviol-Glucosides in Extracts from Stevia rebaudiana Bertoni," Plant Physiol. vol. 95, (1991) 152-156.

Starratt, et al., "Rebaudioside F, a diterpene glycoside from Stevia Rebaudiana", Phytochemistry, vol. 59 2002, 367-370.

Sweet Green Fields, LLC, "Notice to the U.S. Food and Drug Administration (FDA) that the use of Rebiana (Rebaudiosid A) derived from Stevia rebaudiana, as a Food Ingredient is Generally Recognized as Safe (GRAS)," Jan. 15, 2009, http://www.accessdata.fda.gov/scripts/fcn/gras_notices/grn000282.pdf (obtained from the WEB on May 8, 2012) entire document esp. p. 22, Table 1.

Tanaka, O., "Improvement of taste of natural sweeteners", Pure & Appl. Chem., vol. 69, No. 4 1997, 675-683.

Teo, et al., "Validation of green-solvent extraction combined with chromatographic chemical fingerprint to evaluate quality of Stevia rebaudiana Bertoni", J. Sep. Sci, vol. 32 2009, 613-622.

United Nations' Food and Agriculture Organization/Joint Expert Committee on Food Additives (2010) Steviol Glycosides, Compendium of Food Additive Specifications, FAO JECFA Monographs 10, 17-21.

van der Maarel et al., "Properties and applications of starch-converting enzymes of the a-amylase family," Journal of Biotechnology, vol. 94 (2002) 137-155.

Vasquez, Stimulation of the Gerbil's Gustatory Receptors by Some Potently Sweet Terpenoids, J. Agric. Food Chem., vol. 41, 1305-1310, 1993.

Yamamoto, K. et al., "Effective Production of Glycosyl-steviosides by a-1,6 Transglucosylation of Dextrin Dextranase", Biosci. Biotech. Biochem. vol. 58, No. 9 1994, 1657-1661.

Yoda, et al., "Supercritical fluid extraction from Stevia rebaudiana Bertoni using CO2 and CO2+ water: extraction kinetics and identification of extracted components", Journal of Food Engineering, vol. 57 2003, 125-134.

Zell, et al., "Investigation of Polymorphism in Aspartame and Neotame Using Solid-State NMR Spectroscopy", Tetrahedron, vol. 56, 2000, 6603-6616.

Zhang, et al., "Membrane-based separation scheme for processing sweetener from Stevia leaves", Food Research International, vol. 33 2000, 617-620.

a-Glucosyltransferase Treated Stevia, Japan's Specifications and Standards for Food Additives, VIII edition, 2009, p. 257.

Ahmed, et al., "Use of p-Bromophenacyl Bromide to Enhance Ultraviolet Detection of Water-Soluble Organic Acids (Steviolbioside and Rebaudioside B) in High-Performance Liquid Chromatographic Analysis", Journal of Chromatography, vol. 192, 1980, 387-393.

Chang, S. S. et al., "Stability Studies of Stevioside and Rebaudioside A in Carbonated Beverages", Journal of Agricultural and Food Chemistry, vol. 31, 1983, 409-412.

Chen, et al., "Enrichment and separation of rebaudioside A from stevia glycosides by a novel adsorbent with pyridyl group", Science in China, vol. 42, No. 3 1999, 277-282.

Chen, et al., "Selectivity of polymer adsorbent in adsorptive separations of stevia diterpene glycisides", Science in China, vol. 41, No. 4 1998, 436-441.

Chen, et al., "Studies on the adsorptive selectivity of the polar resin with carbonyl group on rebaudioside A", Acta Polymeric Scnica, No. 4 1999, 398-403.

Crammer, et al., "Sweet glycosides from the Stevia plant", Chemistry in Britain, Oct. 1986, 915-916, 918.

Darise et al., "Enzymic Transglucosylation of Rubusoside and the Structure-Sweetness Relationship of Steviol Bisglycosides," Agric. Biol. Chem. vol. 48(10), 1984, 2483-2488.

Dubois et al., "Diterpenoid Sweeteners. Synthesis and Sensory Evaluation of Stevioside Analogues with Improved Organoleptic Properties," J. Med. Chem. vol. 28, (1985) 93-98.

Fuh, , "Purification of steviosides by membrane and ion exchange process", Journal of Food Science, vol. 55, No. 5 1990, 1454-1457.

Fukunaga et al., "Enzymic Transglucosylation Products of Stevioside: Separation and Sweetness-evaluation," Agric. Biol. Chem. vol. 53(6) (1989) 1603-1607.

Fullas et al., "Separation of natural product sweetening agents using overpressured layer chromatography," Journal of Chromatography vol. 464 (1989) 213-219.

Hale, et al., "Amylase of Bacillus Macerans", Cereal Chemistry, vol. 28, No. 1, Jan. 1951, 49-58.

International Search Report and Written Opinion of PCT/US2010/055960.

International Search Report and Written Opinion of PCT/US2011/028028.

International Search Report and Written Opinion of PCT/US2011/033734.

International Search Report and Written Opinion of PCT/US2011/033737.

International Search Report and Written Opinion of PCT/US2011/033912.

International Search Report and Written Opinion of PCT/US2011/035173.

International Search Report and Written Opinion of PCT/US2011/036063, mailed Aug. 5, 2011.

International Search Report and Written Opinion of PCT/US2011/047498, mailed Dec. 22, 2011.

International Search Report and Written Opinion of PCT/US2011/047499, mailed Dec. 22, 2011.

International Search Report and Written Opinion of PCT/US2011/064343.

International Search Report and Written Opinion of PCT/US2012/024585.

International Search Report and Written Opinion of PCT/US2012/024722.

International Search Report and Written Opinion of PCT/US2012/030210.

International Search Report and Written Opinion of PCT/US2012/043294.

International Search Report and Written Opinion of PCT/US2012/051163.

International Search Report and Written Opinion of PCT/US2012/052659.

International Search Report and Written Opinion of PCT/US2012/052665.

International Search Report and Written Opinion of PCT/US2013/030439.

Jaitak, et al., "An Efficient Microwave-assisted Extraction Process of Stevioside and Rebaudioside-A from Stevia Rebaudiana (Bertoni)", Phytochem. Anal. vol. 20 2009, 240-245.

Kennelly, "Sweet and non-sweet constituents of Stevia rebaudiana", Stevia: The genus Stevia, Taylor & Francis, 2002, 68-85.

Kinghorn, "Overview", Stevia: The genus *Stevia*, Taylor & Francis, 2002, 1-17.

Kitahata, S. et al., "Production of Rubusoside Derivatives by Transgalactosylation of Various b-Galactosidases", Agric. Biol. Chem., vol. 53, No. 11 1989, 2923-2928.

Kobayashi, et al., "Dulcoside A and B, New diterpene glycosides from Stevia Rebaudiana", Phytochemistry, vol. 16 1977, 1405-1408.

Kochikyan, et al., "Combined Enzymatic Modification of Stevioside and Rebaudioside A", Applied Biochemistry and Microbiology, vol. 42, No. 1, 2006, 31-37.

Kohda, et al., "New sweet diterpene glucosides from Stevia Rebaudiana", Phytochemistry, vol. 15 1976, 981-983.

Kovylyaeva, et al., "Glycosides from Stevia rebaudiana", Chemistry of Natural Compounds, vol. 43, No. 1 2007, 81-85.

Liu, et al., "Study of stevioside preparation by membrane separation process", Desalination, vol. 83 1991, 375-382.

Lobov, S. V. et al., "Enzymic Production of Sweet Stevioside Derivatives: Transglucosylation of Glucosidases", Agric. Biol. Chem., vol. 55, No. 12 1991, 2959-2965.

Montovaneli, et al., "The effect of temperature and flow rate on the clarification of the aqueous Stevia-extract in fixed-bed column with zeolites", Brazilian Journal of Chemical Engineering, vol. 21, No. 3 2004, 449-458.

(56) References Cited

OTHER PUBLICATIONS

Moraes, et al., "Clarification of Stevia rebaudiana (Bert.) Bertoni extract adsorption in modified zeolites", Acta Scientiarum, vol. 23, No. 6 2001, 1375-1380.

Ohta et al., "Characterization of Novel Steviol Glycosides from Leaves of Stevia rebaudiana Morita," J. Appl. Glycosi., vol. 57, 199-209, 2010.

Ohtani et al. "Chapter 7. Methods to improve the taste of the sweet principles of Stevia rebaudiana." The Genus *Stevia*, edited by A. Douglas Kinghorn, CRC Press 2001, Taylor and Francis, London and New York, pp. 138-159.

Phillips, K. C., "Stevia: steps in developing a new sweetener", In T.H. Grenby, Editor, Developments in Sweeteners-3, Elsevier 1987, 1-43.

Pol, et al., "Comparison of two different solvents employed for pressurised fluid extraction of stevioside from Stevia rebaudiana: methanol versus water", Anal Bioanal Chem vol. 388 2007, 1847-1857.

Prakash et al., "Development of rebiana, a natural, non-caloric sweetener," Jul. 1, 2008, Food and Chemical Toxology, vol. 46, Is. 7, Sup. 1, p. S75-S82.

Richman et al., "Fuctional genomics uncovers three glucosyltransferases involved in the synthesis of the major sweet glucosides of Stevia rebaudiana," The Plant Journal, vol. 41 (2005) 56-67.

Sakamoto et al., "Application of 13C NMR Spectroscopy to Chemistry of Natural Glycosides: Rebaudioside-C, a New Sweet Diterpene Glycoside of Stevia Rebaudiana", Chem. Pharm. Bull., vol. 25, 1977, 844-846.

\* cited by examiner

Rebaudioside B

Steviolbioside

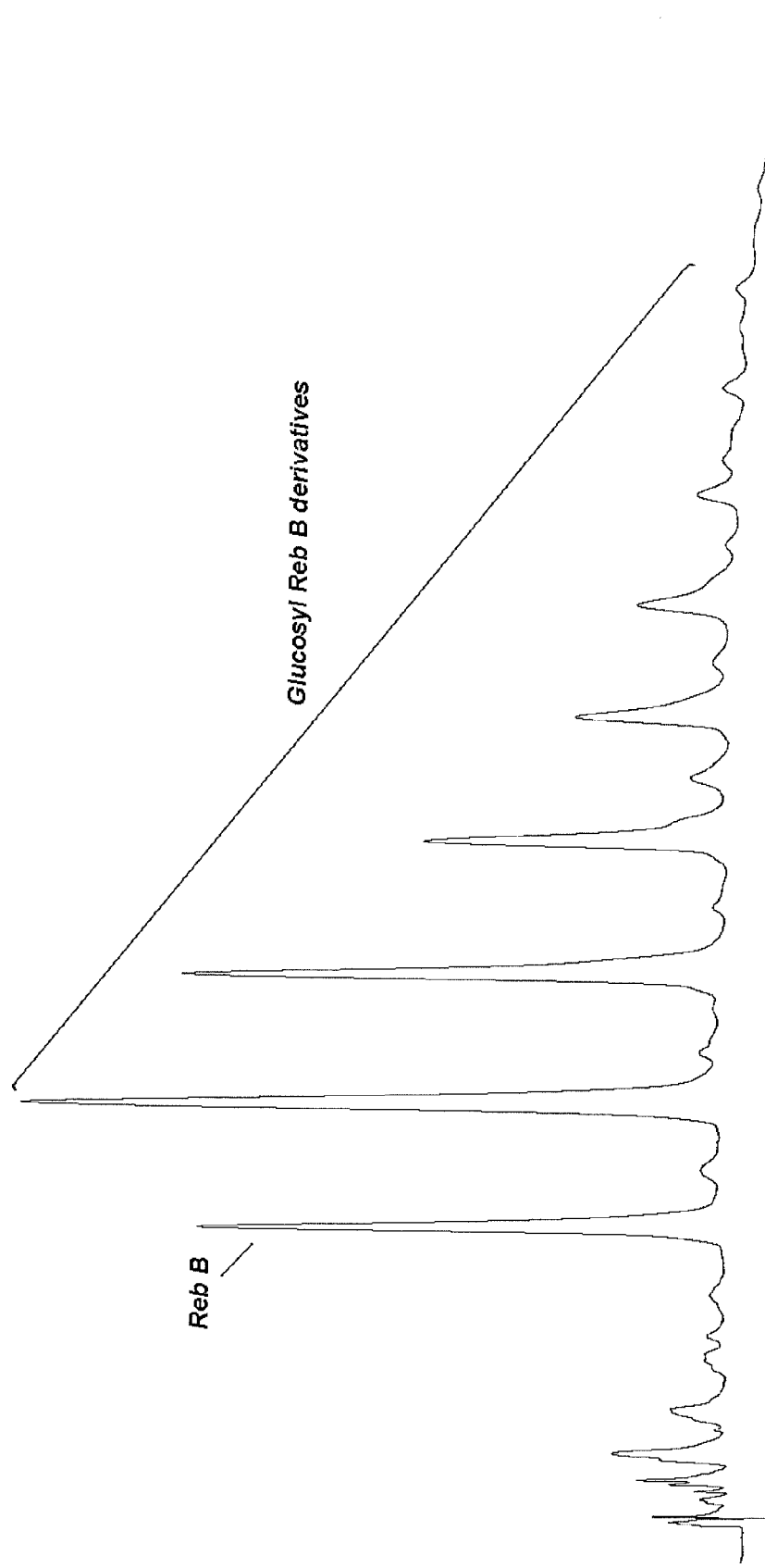

GLUCOSYL STEVIA COMPOSITION

BACKGROUND OF THE INVENTION

1. Field of the Invention

The invention relates to a process for producing a highly purified food ingredient from the extract of the *Stevia rebaudiana* Bertoni plant and its use in various food products and beverages.

2. Description of the Related Art

Nowadays sugar alternatives are receiving increasing attention due to awareness of many diseases in conjunction with consumption of high-sugar foods and beverages. However many artificial sweeteners such as dulcin, sodium cyclamate and saccharin were banned or restricted in some countries due to concerns on their safety. Therefore non-caloric sweeteners of natural origin are becoming increasingly popular. The sweet herb *Stevia rebaudiana* Bertoni, produces a number of diterpene glycosides which feature high intensity sweetness and sensory properties superior to those of many other high potency sweeteners.

The above-mentioned sweet glycosides, have a common aglycon, steviol, and differ by the number and type of carbohydrate residues at the C13 and C19 positions. The leaves of Stevia are able to accumulate up to 10-20% (on dry weight basis) steviol glycosides. The major glycosides found in Stevia leaves are rebaudioside A (2-10%), stevioside (2-10%), and rebaudioside C (1-2%). Other glycosides such as rebaudioside B, D, E, and F, steviolbioside and rubusoside are found at much lower levels (approx. 0-0.2%).

Two major glycosides—stevioside and rebaudioside A, were extensively studied and characterized in terms of their suitability as commercial high intensity sweeteners. Stability studies in carbonated beverages confirmed their heat and pH stability (Chang S. S., Cook, J. M. (1983) Stability studies of stevioside and rebaudioside A in carbonated beverages. *J. Agric. Food Chem.* 31: 409-412.)

Steviol glycosides differ from each other not only by molecular structure, but also by their taste properties. Usually stevioside is found to be 110-270 times sweeter than sucrose, rebaudioside A between 150 and 320 times, and rebaudioside C between 40-60 times sweeter than sucrose. Dulcoside A is 30 times sweeter than sucrose. Rebaudioside A has the least astringent, the least bitter, and the least persistent aftertaste thus possessing the most favorable sensory attributes in major steviol glycosides (Tanaka O. (1987) Improvement of taste of natural sweetners. *Pure Appl. Chem.* 69:675-683; Phillips K. C. (1989) Stevia: steps in developing a new sweetener. In: Grenby T. H. ed. Developments in sweeteners, vol. 3. Elsevier Applied Science, London. 1-43.)

Methods for the extraction and purification of sweet glycosides from the *Stevia rebaudiana* plant using water or organic solvents are described in, for example, U.S. Pat. Nos. 4,361,697; 4,082,858; 4,892,938; 5,972,120; 5,962,678; 7,838,044 and 7,862,845.

However, even in a highly purified state, steviol glycosides still possess undesirable taste attributes such as bitterness, sweet aftertaste, licorice flavor, etc. One of the main obstacles for the successful commercialization of stevia sweeteners are these undesirable taste attributes. It was shown that these flavor notes become more prominent as the concentration of steviol glycosides increases (Prakash I., DuBois G. E., Clos J. F., Wilkens K. L., Fosdick L. E. (2008) Development of rebiana, a natural, non-caloric sweetener. Food Chem. Toxicol., 46, S75-S82.)

Some of these undesirable properties can be reduced or eliminated by subjecting steviol glycosides to the reaction of intermolecular transglycosylation, when new carbohydrate residues are attached to initial molecule at glycosidic moieties linked to C13 and C19 positions of steviol. Depending on the number of carbohydrate residues in these positions the quality and potency of the compounds taste will vary.

Pullulanase, isomaltase (Lobov S. V., Jasai R., Ohtani K., Tanaka O. Yamasaki K. (1991) Enzymatic production of sweet stevioside derivatives: transglycosylation by glucosidases. *Agric. Biol. Chem.* 55: 2959-2965), β-galactosidase (Kitahata S., Ishikawa S., Miyata T., Tanaka O. (1989) Production of rubusoside derivatives by transglycosylation of various β-galactosidase. *Agric. Biol. Chem.* 53: 2923-2928), and dextran saccharase (Yamamoto K., Yoshikawa K., Okada S. (1994) Effective production of glucosyl-stevioside by $\alpha$-1,6-transglucosylation of dextran dextranase. *Biosci. Biotech. Biochem.* 58: 1657-1661) have been used as transglycosylating enzymes, together with pullulan, maltose, lactose, and partially hydrolyzed starch, respectively, as donors of glycosidic residues.

The transglucosylation of steviol glycosides was also performed by action of cyclodextrin glucanotransferases (CGTase) produced by *Bacillus stearothermophilus* (U.S. Pat. Nos. 4,219,571, and 7,807,206) as a result $\alpha$-1,4-glucosyl derivatives were formed with degree of polymerization up to 10.

It has to be noted that in above-mentioned process $\alpha$-1,4-glucosylation occurs at glycosidic moieties linked to C13 and C19 position of steviol. On the other hand, it was described by Fukunaga et al. (1989) that the derivatives with $\alpha$-1,4-glucosyl residues at C13 position of steviol possess superior taste characteristics compared to those with $\alpha$-1,4-glucosyl moieties attached to C19 position of steviol. (Fukunaga Y., Miyata T., Nakayasu N., Mizutani K., Kasai R., Tanaka O. (1989) *Enzymic Transglucosylation Products of Stevioside: Separation and Sweetness-evaluation*, Agric. Biol. Chem., 53 (6), 1603-1607).

It is also to be noted that two naturally occurring steviol glycosides, namely steviolbioside (CAS No. 41093-60-1) and rebaudioside B (CAS No. 58543-17-2) do not have glycosidic moieties attached to C19 position. Therefore their $\alpha$-1,4-glucosylation will produce exclusively derivatives with $\alpha$-1,4-glucosyl residues attached to carbohydrate moieties of C13 position of steviol. However a commercially viable process for producing such derivatives is not available due to low solubility of steviolbioside and rebaudioside B (reb B).

No information on taste properties and functionality of $\alpha$-1,4-glucosylated steviolbioside and reb B is available as well.

Therefore to provide a glucosyl stevia with the best combination of sweetness potency and flavor profile it is necessary to develop highly purified glucosyl stevia products containing derivatives with the most desirable taste characteristics.

SUMMARY OF THE INVENTION

The present invention is aimed to overcome the disadvantages of existing Stevia sweeteners. The invention describes a process for producing a high purity food ingredient from the extract of the *Stevia rebaudiana* Bertoni plant and use thereof in various food products and beverages as a sweetness and flavor modifier.

The invention, in part, pertains to an ingredient comprising glucosylated derivatives of steviol glycosides of *Stevia* rebaudiana Bertoni plant. The steviol glycosides are selected from the group consisting of rebaudioside B, steviolbioside, steviolmonoside, as well as other steviol glycosides found in *Stevia rebaudiana* Bertoni plant and mixtures thereof.

The invention, in part, pertains to a process for producing an ingredient containing glucosylated forms of rebaudioside B, steviolbioside, steviolmonoside, as well as other steviol glycosides found in *Stevia rebaudiana* Bertoni plant. The process can be an enzymatic transglucosylation process using CGTases produced by cultures of *Bacillus stearothermophilus*. The process can also have a step of post-transglucosylation enzymatic treatment using various glucosidases. The process can also have the steps of decolorizing, desalting and removing dextrins and various impurities. The decolorizing can be performed using activated carbon. The desalting can be performed by passing through ion exchange resins and/or membrane filters. Removing the dextrins and impurities can be performed by passing through macroporous polymeric resin.

In the invention, steviolbioside or reb B commercialized by PureCircle Sdn. Bhd. (Malaysia), with purity of at least 95%, was used as a starting material. Alternatively starting materials with different content and ratio of steviolbioside, reb B, and/or other steviol glycosides may be used as well.

The starting material was converted into freely soluble form, and then subjected to enzymatic transglucosylation by action of cyclodextrin glycosyltransferase (CGTase) in the presence of starch as a glucose donor. As a result α-1,4-glucosyl derivatives (C13) of initial steviol glycoside were formed.

The unreacted steviol glycoside was precipitated from reaction mixture while the other impurities were removed by Amberlite XAD7 HP resin, and then purified reaction mixture was decolorized, concentrated and spray dried.

The obtained products were applied in various foods and beverages as sweeteners, sweetener enhancers and flavor modifiers, including ice cream, cookies, bread, fruit juices, milk products, baked goods and confectionary products.

It is to be understood that both the foregoing general description and the following detailed description are exemplary and explanatory and are intended to provide further explanation of the invention as claimed.

BRIEF DESCRIPTION OF THE DRAWINGS

FIG. 3 shows the HPLC chromatogram of reaction mixture after residual reb B precipitation step

DETAILED DESCRIPTION OF THE INVENTION

Figure 1A:
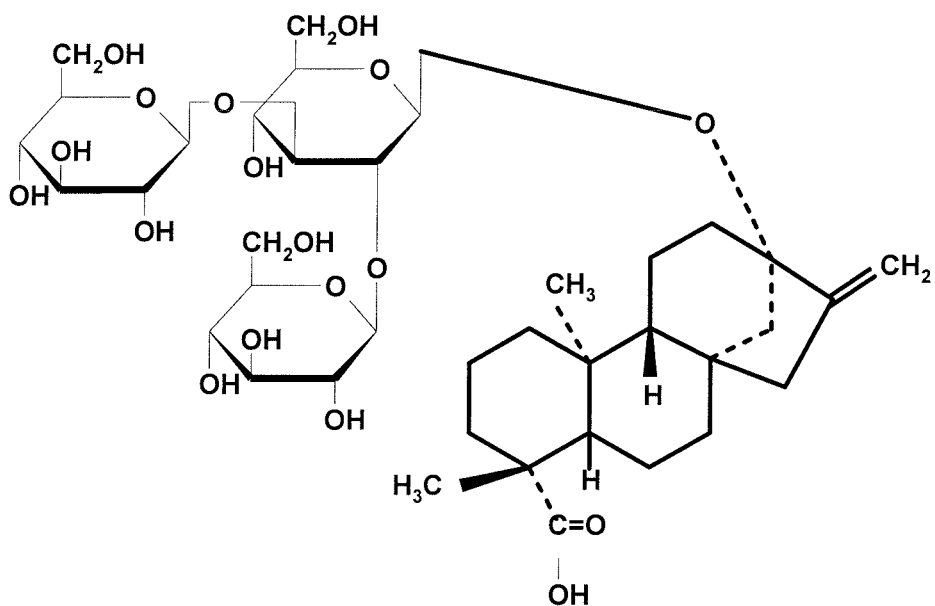
FIGS. 1a and 1b show the structure of reb B and steviolbioside
Figure 1B:
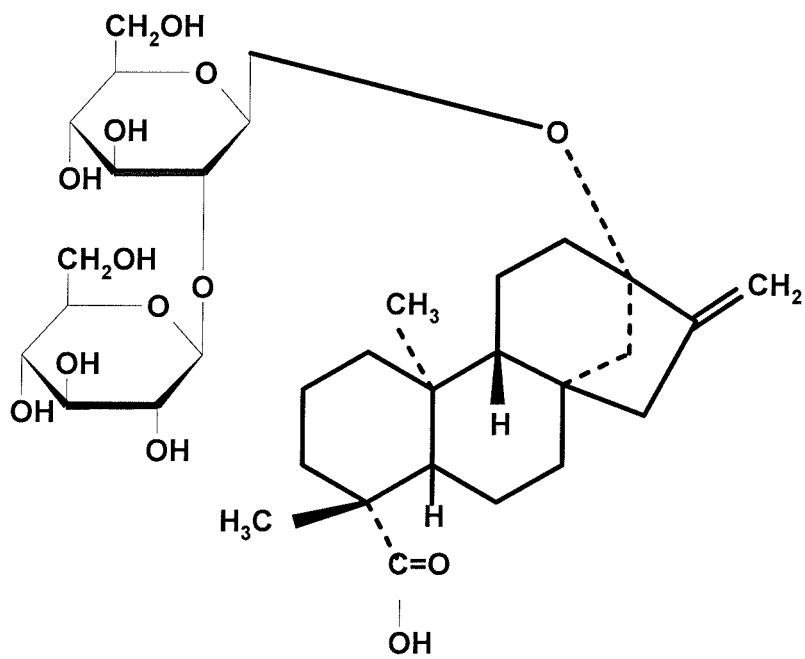
Figure 2:
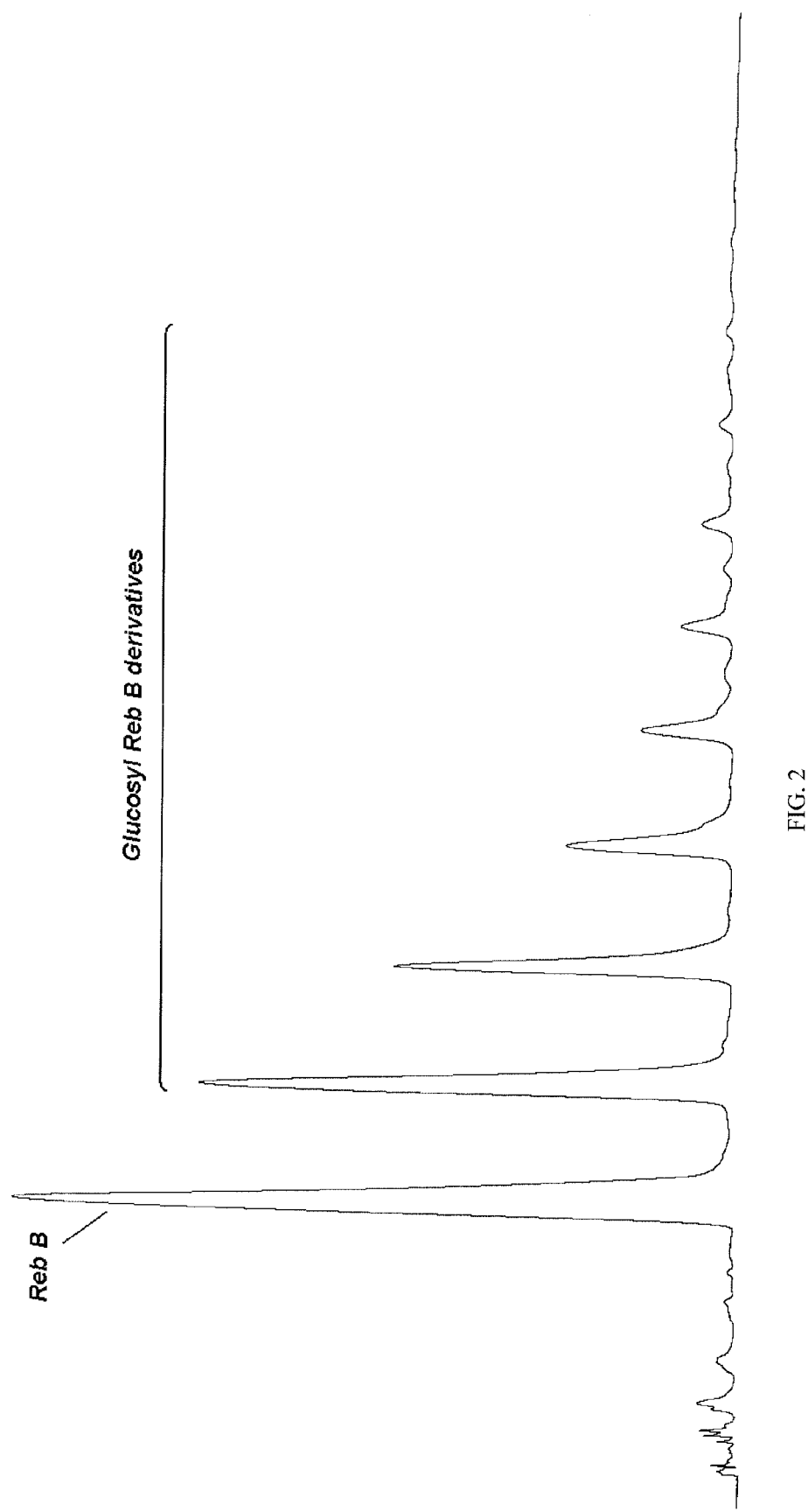
FIG. 2 shows the HPLC chromatogram of reaction mixture containing reb B and its glucosyl derivatives after glucosylation step

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In one embodiment of present invention highly purified reb B commercialized by PureCircle Sdn. Bhd. (Malaysia), containing reb B (>95%), reb A (<5%), and other glycosides amounting to total steviol glycosides content of at least 97%, was used as a starting material. Alternatively starting materials with different content and ratio of steviolbioside, reb B, and/or other steviol glycosides may be used as well.

The HPLC analysis of the raw materials and products was performed on Agilent Technologies 1200 Series (USA) liquid chromarograph, equipped with Zorbax-$NH_2$ (4.6×250 mm) column. The mobile phase was acetonitrile-water gradient from 70:30, v/v (0-2 min) to 50:50, v/v (2-70 min). A diode array detector set at 210 nm was used as the detector.

Hereinafter the terms describing the material solubility such as "slightly soluble" "freely soluble" etc are given according to definitions provided in FAO JECFA Monographs 1 (2006), Combined Compendium of Food Additive Specifications, vol. 4, page 41.

Due to fact that reb B (and steviolbioside) is slightly soluble in water, it is not possible to introduce it to reaction mixture "as-is". Therefore the reb B is converted to freely soluble form. Reb B is suspended in 1-3 volumes, preferably in 1.2-1.6 volumes of water. The suspension is heated to 50-100° C., preferably 60-90° C. under continuous agitation. NaOH is added to the suspension to reach a pH value of about 6.0-9.0, preferably 7.0-8.0. Alternatively KOH or other alkalis may be used. Addition of alkali ensures complete dissolution of reb B (and steviolbioside), which is otherwise almost insoluble in water even at temperatures exceeding 100° C. After complete dissolution the obtained solution is spray dried to yield a freely soluble form of reb B. Similar technique may be used for preparation of freely soluble form of steviolbioside.

The transglucosylation was accomplished by cyclomaltodextrin glucanotransferases (CGTases; EC 2.4.1.19) produced by *Bacillus stearothermophilus* St-88 (PureCircle Sdn Bhd Collection of Industrial Microorganisms—Malaysia). However, any other CGTase or enzyme possessing intermolecular transglucosylation activity may be applied as well. The enzyme can be in a form of cell-free culture broth, concentrated liquid cell-free culture broth, spray dried or freeze dried cell-free culture broth, or high purity protein. Free and immobilized enzyme preparations can be used.

The activity of CGTase preparations was determined according to the procedure described in Hale W. S., Rawlins L. C. (1951) Amylase of *Bacillus macerans*. Cereal Chem. 28, 49-58.

Starches of different origin may be used as donors of glucosyl units such as, derived from wheat, corn, potato, tapioca, and sago.

Starch was subjected to partial hydrolysis (liquefaction) prior to the transglycosylation reaction. The dextrose equivalent of the partially hydrolyzed starch can be in the range of about 10-25, preferably about 12-16. Any enzyme capable of starch hydrolysis may be used for liquefaction, such as α-amylases, β-amylases etc. In one embodiment, CGTase and α-amylase mixtures as liquefying enzymes are preferred.

α-Amylase activity is expressed in Kilo Novo α-amylase Units (KNU). One KNU is the amount of α-amylase which, under standard conditions (pH 7.1; 37° C.), dextrinizes 5.26 g starch dry substance per hour.

The liquefaction mixture contains about 0.001-0.2 KNU, preferably about 0.05-0.1 KNU of α-amylase per one unit of CGTase.

The use of α-amylase in liquefaction allows achieving higher throughputs in further activated carbon filtration. When the CGTase is used as the only liquefying enzyme the filtration rate is approximately 10-15 L/hr per 1 $m^2$ of filter surface. In case of liquefaction enzyme mixture (comprising α-amylase and CGTase) the filtration rate is twice as fast—approximately 20-30 L/hr per 1 m² of filter surface.

The ratio of starch and CGTase in the liquefaction mixture is about 0.1-0.5 units per one gram of starch, preferably about 0.2-0.4 units per gram.

The concentration of starch in liquefaction mixture is about 15-40% (wt/wt), preferably about 20-30%.

The liquefaction is conducted at about 70-90° C. during about 0.5-5 hours, preferably about 1-2 hours.

After liquefaction, the reaction mixture is subjected to thermal inactivation of α-amylase at low pH conditions. The preferred pH range for inactivation is about pH 2.5 to pH 3.0 and preferred temperature is about 95-105° C. The duration of thermal inactivation is about 5-10 minutes.

After the inactivation, the pH of the reaction mixture is adjusted to about pH 5.5-6.5 and the freely soluble reb B is added to the mixture and dissolved. The preferred ratio of reb B to starch (kg of steviol glycoside per 1 kg of starch) is about 0.5-1.5, preferably about 0.8-1.2.

A second portion of CGTase preparation is added and the transglucosylation reaction is conducted at about 65° C. for about 24-48 hours. The amount of the second portion of CGTase is about 0.2-4 units of CGTase per gram of solids, preferably about 0.5-1.2 units per gram of solids.

Upon completion of transglucosylation reaction, the reaction was stopped by heating at about 95° C. for about 15 minutes to inactivate the CGTase, then the solution was treated with activated carbon, to obtain decolorized reaction mixture. The amount of activated carbon was about 0.02-0.4 grams per gram of solids, preferably about 0.05-0.2 grams per gram of solids.

The decolorized reaction mixture was cooled to 5° C. and the pH was adjusted by $H_3PO_4$ to pH 2.0-4.5, preferably 3.0-4.0. The mixture was held under moderate agitation for 24 hrs, which resulted in precipitation of unreacted reb B. The precipitated reb B was separated by filtration and the pH of filtrate containing mainly α-1,4-glucosyl derivatives (C13) was adjusted to 5.0-7.0, preferably 6.0-6.5.

The impurities were removed using Amberlite XAD7 HP. The steviol glycosides and their glucosylated derivatives were adsorbed on the resin and subsequently eluted by aqueous ethanol. The resulted aqueous ethanol eluate, containing glucosyl steviol glycosides, was subsequently decolorized as described above and the glycosides solution, after the evaporation of eluting solvent, was powdered by spray drying.

The sensory assessment of glucosyl reb B sample ("Invention Sample") in comparison with commercial glucosyl stevia sample was carried using aqueous solutions, with 20 panelists. Based on overall acceptance the most desirable samples were chosen. The results are shown in Table 1.

TABLE 1

Sensory assessment of samples in water system

| Judgment | Commercial glucosyl stevia | Invention Sample |
|---|---|---|
| Most desirable | 2 | 18 |
| Sweetness power (5% sucrose) | 120 | 150 |
| Comments | Sweet, slightly bitter, astringent, lingering aftertaste, sweetness onset is slow | Sweet, light, soft, round, pleasant, similar to sucrose, no lingering aftertaste, sweetness onset is rapid |

As apparent from the results in Table 1, the sweetness quality of the glucosyl reb B composition was rated as more superior.

Glucosyl reb B composition had higher sweetness power (150 times sweeter compared to a 5% sucrose solution).

The compositions of this invention can be used as sweetness enhancers, flavor enhancers and sweeteners in various food and beverage products. Non-limiting examples of food and beverage products include carbonated soft drinks, ready to drink beverages, energy drinks, isotonic drinks, low-calorie drinks, zero-calorie drinks, sports drinks, teas, fruit and vegetable juices, juice drinks, dairy drinks, yoghurt drinks, alcohol beverages, powdered beverages, bakery products, cookies, biscuits, baking mixes, cereals, confectioneries, candies, toffees, chewing gum, dairy products, flavored milk, yoghurts, flavored yoghurts, cultured milk, soy sauce and other soy base products, salad dressings, mayonnaise, vinegar, frozen-desserts, meat products, fish-meat products, bottled and canned foods, tabletop sweeteners, fruits and vegetables.

Additionally the compositions can be used in drug or pharmaceutical preparations and cosmetics, including but not limited to toothpaste, mouthwash, cough syrup, chewable tablets, lozenges, vitamin preparations, and the like.

The compositions can be used "as-is" or in combination with other sweeteners, flavors and food ingredients.

Non-limiting examples of sweeteners include steviol glycosides, stevioside, rebaudioside A, rebaudioside B, rebaudioside C, rebaudioside D, rebaudioside E, rebaudioside F, dulcoside A, steviolbioside, rubusoside, as well as other steviol glycosides found in *Stevia rebaudiana* Bertoni plant and mixtures thereof, stevia extract, Luo Han Guo extract, mogrosides, high-fructose corn syrup, corn syrup, invert sugar, fructooligosaccharides, inulin, inulooligosaccharides, coupling sugar, maltooligosaccharides, maltodextrins, corn syrup solids, glucose, maltose, sucrose, lactose, aspartame, saccharin, sucralose, sugar alcohols.

Non-limiting examples of flavors include lemon, orange, fruity, banana, grape, pear, pineapple, bitter almond, cola, cinnamon, sugar, cotton candy, vanilla flavors.

Non-limiting examples of other food ingredients include flavors, acidulants, organic and amino acids, coloring agents, bulking agents, modified starches, gums, texturizers, preservatives, antioxidants, emulsifiers, stabilisers, thickeners, gelling agents.

The following examples illustrate various embodiments of the invention. It will be understood that the invention is not limited to the materials, proportions, conditions and procedures set forth in the examples, which are only illustrative.

Example 1

Preparation of CGTase

A strain of *Bacillus stearothermophilus* St-88 was inoculated in 2,000 liters of sterilized culture medium containing 1.0% starch, 0.25% corn extract, 0.5% $(NH_4)_2SO_4$, and 0.2% $CaCO_3$ (pH 7.0-7.5) at 56° C. for 24 hrs with continuous aeration (2,000 L/min) and agitation (150 rpm). The obtained culture broth was filtered using Kerasep 0.1 μm ceramic membrane (Novasep, France) to separate the cells. The cell-free permeate was further concentrated 2-fold on Persep 10 kDa ultrafilters (Orelis, France). The activity of the enzyme was determined according to Hale, Rawlins (1951). A crude enzyme preparation with activity of about 2 unit/mL was obtained.

Example 2

Preparation of Freely Soluble Reb B 1,000 g of reb B produced by PureCircle Sdn Bhd containing 97.1% reb B, 2.5% reb A, was suspended in 1,500 mL of water. The suspension was placed under agitator and heated to 80° C. 50% NaOH solution was added to the suspension till the pH reached 8.0. The suspension was agitated for 1 hr until complete dissolution. The obtained solution was dried using YC-015 laboratory spray drier (Shanghai Pilotech Instrument & Equipment Co. Ltd., China) operating at 175° C. inlet and 100° C. outlet temperature. 990 g amorphous powder was obtained with 40% (w/v) solubility in water (at 25° C.).

Example 3

Preparation of Glucosyl Stevia Composition 100 g of tapioca starch was suspended in 300 mL of water (pH 6.5). 2 KNU of α-amylase (Termamyl Classic, Novozymes, Denmark) and 30 units of CGTase obtained according to EXAMPLE 1 were added, and the liquefaction of starch was carried out at 80° C. for about one hour to dextrose equivalent about 15. The pH of reaction mixture was adjusted to pH 2.8 by hydrochloric acid and the mixture was boiled at 100° C. during 5 minutes to inactivate the enzymes. After cooling to 65° C., the pH was adjusted to pH 6.0 with sodium hydroxide solution. 100 g freely soluble reb B obtained according to EXAMPLE 2 was added to liquefied starch and stirred until a homogeneous solution was obtained. 200 units of CGTase was added to the solution and the mixture was held at a temperature of 65° C. for 24 hours under continuous agitation. The obtained reaction mixture was heated at 95° C. for 15 minutes to inactivate the enzyme. After cooling to 65° C., 20 grams of activated carbon was added and the mixture was heated to 75° C. and held for 30 minutes. The mixture was filtered, the filtrate was cooled to 5° C. and the pH was adjusted to pH 3.5 with $H_3PO_4$. The filtrate was held under moderate agitation for 24 hrs. Then the precipitated crystals were filtered and the pH of obtained solution was adjusted to pH 6.5. the solution was diluted with water to 5% solids content and passed through column packed with 4000 mL Amberlite XAD 7 HP macroporous adsorbent resin. The column was washed with 5 volumes of water and 2 volumes of 20% (v/v) ethanol. The adsorbed glycosides were eluted with 50% ethanol. The ethanol was evaporated and the desalted and decolorized water solution was concentrated at 60° C. under vacuum, then dried into a powder form using laboratory spray dryer. 151 grams of product was obtained.

Example 4

Low-Calorie Orange Juice Drink

Orange concentrate (35%), citric acid (0.35%), ascorbic acid (0.05%), orange red color (0.01%), orange flavor (0.20%), rebaudioside A (0.003%) and different glucosyl stevia compositions (0.03%) were blended and dissolved completely in water (up to 100%) and pasteurized. Glucosyl stevia compositions were represented by commercial glucosyl stevia and a sample obtained according to EXAMPLE 3.

The sensory evaluations of the samples are summarized in Table 2. The data show that the best results can be obtained by using the highly purified glucosyl stevia composition of EXAMPLE 3. Particularly the drinks prepared with EXAMPLE 3 sample exhibited a rounded and complete flavor profile and mouthfeel.

TABLE 2

Evaluation of orange juice drink samples

| Sample | Flavor | Aftertaste | Mouthfeel |
|---|---|---|---|
| Commercial | Sweet, licorice notes | Slight bitterness and aftertaste | Not acceptable |
| EXAMPLE 3 | High quality sweetness, pleasant taste similar to sucrose, rounded and balanced flavor | Clean, no bitterness and no aftertaste | Full |

The same method can be used to prepare juices and juice drinks from other fruits, such as apples, lemons, apricots, cherries, pineapples, mangoes, etc.

Example 5

Low-Calorie Carbonated Beverage

A carbonated beverage according to formula presented below was prepared.

| Ingredients | Quantity, % |
|---|---|
| Sucrose | 5.5 |
| Cola flavor | 0.340 |
| ortho-Phosphoric acid | 0.100 |
| Sodium citrate | 0.310 |
| Sodium benzoate | 0.018 |
| Citric acid | 0.018 |
| Rebaudioside A | 0.003 |
| Glucosyl stevia composition | 0.05 |
| Carbonated water | to 100 |

The sensory properties were evaluated by 20 panelists. The results are summarized in Table 3.

TABLE 3

Evaluation of low-calorie carbonated beverage samples

| | Number of panelists detected the attribute | |
|---|---|---|
| Taste attribute | Commercial Sample | EXAMPLE 3 |
| Bitter taste | 17 | 0 |
| Astringent taste | 16 | 0 |
| Aftertaste | 18 | 0 |
| Comments | | |
| Quality of sweet taste | Bitter aftertaste (16 of 20) | Clean (20 of 20) |
| Overall evaluation | Satisfactory (1 of 20) | Satisfactory (20 of 20) |

The above results show that the beverage prepared using EXAMPLE 3 sample possessed the best organoleptic characteristics.

Example 6

Diet Cookies

Flour (50.0%), margarine (30.0%) fructose (10.0%), maltitol (8.0%), whole milk (1.0%), salt (0.2%), baking powder (0.15%), vanillin (0.1%) and different glucosyl stevia compositions (0.03%) were kneaded well in dough-mixing machine. The obtained dough was molded and baked in oven at 200° C. for 15 minutes. Glucosyl stevia compositions were represented by commercial glucosyl stevia and a sample obtained according to EXAMPLE 3.

The sensory properties were evaluated by 20 panelists. The best results were obtained in samples prepared by highly purified glucosyl stevia composition (EXAMPLE 3). The panelists noted rounded and complete flavor profile and mouthfeel in cookies prepared with EXAMPLE 3 sample.

Example 7

Yoghurt

Different glucosyl stevia compositions (0.03%) and sucrose (4%) were dissolved in low fat milk. Glucosyl stevia compositions were represented by commercial glucosyl stevia and a sample obtained according to EXAMPLE 3. After pasteurizing at 82° C. for 20 minutes, the milk was cooled to 37° C. A starter culture (3%) was added and the mixture was incubated at 37° C. for 6 hours then at 5° C. for 12 hours.

The sensory properties were evaluated by 20 panelists. The best results were obtained in samples prepared by highly purified glucosyl stevia composition (EXAMPLE 3). The panelists noted rounded and complete flavor profile and mouthfeel in sample prepared with EXAMPLE 3 Sample.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

I claim:

1. A process for producing a highly purified glucosyl stevia composition, comprising the steps of:
   adding starch into water to form a starch suspension;
   adding a mixture of α-amylase and CGTase into the starch suspension and incubating for about 0.5 to 2 hours at about 75-80° C., resulting in a liquefied starch suspension;
   inactivating the α-amylase by low pH heat treatment;
   cooling the liquefied starch suspension and adjusting the pH to about 5.5 to 7.0;
   adding a freely soluble form of steviol glycosides selected from the group consisting of rebaudioside B and steviolbioside into the liquefied starch suspension, resulting in a reaction mixture;
   adding a second batch of CGTase into the reaction mixture and incubating for about 12 to 48 hours at about 55-75° C.;
   inactivating the CGTase by low heat treatment;
   decolorizing the reaction mixture;
   cooling the reaction mixture and adjusting the pH to about 2.0 to 4.5;
   precipitating the unreacted steviol glycosides;
   separating the precipitated unreacted steviol glycosides crystal from filtrate;
   adjusting the pH of filtrate to about 5.5 to 7.0;
   removing impurities by contacting the filtrate with macroporous adsorbent resin and subsequently eluting adsorbed diterpene glycosides with aqueous ethanol to result in a glycoside-containing aqueous ethanol eluate;
   removing ethanol from the aqueous ethanol eluate, resulting in an aqueous eluate; and
   concentrating and drying the aqueous eluate to obtain the highly purified glucosyl stevia composition, wherein the highly purified glucosyl stevia composition comprises derivatives containing α-1,4-glucosyl residues attached to glycosidic residues of C13 position of steviol, and unmodified steviol glycosides.

2. The process according to claim 1, wherein the mixture of α-amylase and CGTase contains about 0.001-0.2 KNU of α-amylase per one unit of CGTase.

3. The process of claim 2, wherein the mixture of α-amylase and CGTase contains about 0.05-0.1 KNU of α-amylase per one unit of CGTase.

4. The process according to claim 1, wherein the weight of added steviol glycosides is about equal to that of the starch.

5. The process according to claim 1, wherein the CGTase is produced by cultures of *Bacillus stearothermophilus*.

6. The process according to claim 1, wherein the second batch of CGTase has about 0.2-4 units of CGTase per gram of solids.

7. The process according to claim 1, wherein the second batch of CGTase has about 0.5-1.2 units of CGTase per gram of solids.

8. The process according to claim 1, wherein the decolorizing is performed using activated carbon.

9. The process according to claim 1, wherein the decolorizing is performed using ion exchange resins or membranes, said membranes being selected from the group consisting of ultrafiltration, nanofiltration, and reverse osmosis membranes.

10. The process of claim 1, wherein removing impurities is conducted with a plurality of sequentially connected columns packed with a macroporous adsorbent resin, followed by washing the columns with water, then washing with about 10-50% (v/v) ethanol, disconnecting the columns, and then eluting each column individually with 30-100% ethanol.

11. The process according to claim 1, wherein the highly purified glucosyl stevia composition has at least about 90% total steviol glycosides on an anhydrous basis.

12. The process according to claim 1 wherein the freely soluble form of steviol glycosides is prepared in a process comprising the steps of:
   providing a slightly soluble form of steviol glycosides selected from the group consisting of rebaudioside B and steviolbioside:
   adding the steviol glycosides to water to form a suspension;
   adding alkali to the suspension to adjust the pH to about pH 6.0 to pH 9.0;
   heating the suspension to about 50-100° C. to obtain a solution of steviol glycoside; and
   spray drying the solution to obtain freely soluble form of steviol glycosides.

* * * * *